United States Patent
Russo et al.

(10) Patent No.: US 10,144,707 B2
(45) Date of Patent: Dec. 4, 2018

(54) TRITIATED NITROXIDES AND USES THEREOF

(71) Applicants: Johnny Russo, Spencerville, MD (US); Gerald M. Rosen, Rockville, MD (US); David I. Bigio, Rockville, MD (US)

(72) Inventors: Johnny Russo, Spencerville, MD (US); Gerald M. Rosen, Rockville, MD (US); David I. Bigio, Rockville, MD (US)

(73) Assignee: ORGANIC ENERGY DEVICES (OED), Baltimore, MD (US)

( * ) Notice: Subject to any disclaimer, the term of this patent is extended or adjusted under 35 U.S.C. 154(b) by 0 days.

(21) Appl. No.: 15/912,121

(22) Filed: Mar. 5, 2018

(65) Prior Publication Data
US 2018/0297947 A1    Oct. 18, 2018

Related U.S. Application Data

(60) Provisional application No. 62/467,943, filed on Mar. 7, 2017.

(51) Int. Cl.
*C07D 207/46* (2006.01)
*H01L 31/04* (2014.01)
*C07B 59/00* (2006.01)
*G21H 1/02* (2006.01)
*H02J 7/00* (2006.01)

(52) U.S. Cl.
CPC .......... *C07D 207/46* (2013.01); *C07B 59/002* (2013.01); *G21H 1/02* (2013.01); *H01L 31/04* (2013.01); *C07B 2200/05* (2013.01); *H02J 7/0052* (2013.01)

(58) Field of Classification Search
CPC .... C07B 59/002; C07B 2200/05; G21H 1/02; H01L 31/04; C07D 207/46
USPC ....................................................... 548/537
See application file for complete search history.

(56) References Cited

U.S. PATENT DOCUMENTS

| | | | | |
|---|---|---|---|---|
| 3,334,103 A * | 8/1967 | Feldman | .............. | C07D 207/46 252/401 |
| 3,502,692 A * | 3/1970 | Feldman | .............. | C07D 207/46 252/401 |
| 4,834,964 A * | 5/1989 | Rosen | .................. | C07D 207/46 424/9.33 |
| 4,845,090 A * | 7/1989 | Gries | ...................... | A61K 49/20 424/9.33 |
| 5,104,641 A * | 4/1992 | Rosen | .................... | A61K 49/20 424/9.33 |
| 5,256,397 A * | 10/1993 | Rosen | .................... | A61K 49/20 424/9.33 |
| 5,431,901 A * | 7/1995 | Halpern | ................. | A61K 49/20 424/9.33 |
| 8,466,130 B2 * | 6/2013 | Zarling | ................ | A61K 31/445 514/89 |
| 2011/0059922 A1 * | 3/2011 | Zarling | ................ | A61K 31/445 514/89 |
| 2011/0165087 A1 * | 7/2011 | Kao | ....................... | A61B 5/055 424/9.33 |

FOREIGN PATENT DOCUMENTS

| | | | | |
|---|---|---|---|---|
| CA | 2468831 A1 * | 7/2003 | .......... | C07D 207/46 |
| EP | 1132085 A1 * | 9/2001 | ............. | A61K 31/40 |
| EP | 1541552 A1 * | 6/2005 | ............. | C07B 41/06 |
| JP | 2000166595 A * | 6/2000 | ............... | C12Q 1/26 |
| WO | WO-8705222 A1 * | 9/1987 | .......... | C07D 207/46 |
| WO | WO-9900365 A1 * | 1/1999 | ......... | A61K 49/0002 |
| WO | WO-2009158698 A2 * | 12/2009 | ........ | G02B 27/1013 |

OTHER PUBLICATIONS

Eriksson et al. Magnetic Resonance in Medicine (1987), 5(1), 73-77 (Year: 1987).*
Colloids and Surfaces, A: Physicochemical and Engineering Aspects (2001), 183-185, 767-776 (Year: 2001).*
Nakken et al. FEBS Letters, vol. 8(1), 33-36 (1970) (Year: 1970).*
Dupuis P. Nouveau Journal de Chimie, vol. 9(5), pp. 375-378 1985 (Year: 1985).*
Neiman L "Facile Method for Preparing Radioactive Nitroxyl Radicals" Bioorganicheskaya Khimiya, vol. 11(3), pp. 414-416 (1985) (Year: 1985).*
Wold, E. et al. International Journal of Radiation Biology and Related Studies in Physics, Chemistry and Medicine / Int. J. Radiat. Biol., vol. 25(3), pp. 225-233 (Year: 1974).*

* cited by examiner

*Primary Examiner* — Nyeemah A Grazier
(74) *Attorney, Agent, or Firm* — Fish IP Law, LLP (57) ABSTRACT

Long-term and high-density energy sources are described that utilize radioisotope batteries that provide a tritium ($^3$H)-based direct energy conversion system. The beta radiation source is a nitroxide compound with a synthetic yield near 100%. The nitroxide compound can be molded into flexible films to cover multiple structures, and has a specific activity and gravimetric density (wt % $^3$H) comparable to that of tritiated hydrides. A carrier system based on such tritiated nitroxides can be scaled up without significant beta self-absorption, permitting the energy source to have higher specific volume power densities than current radioisotope batteries. Such a carrier can be applied directly to a semiconductor array (such as an integrated circuit) in order to provide electrical power or, alternatively, be prepared with a phosphor and applied to a photovoltaic cell.

23 Claims, 8 Drawing Sheets

TRITIATED NITROXIDES AND USES THEREOF

This application claims the benefit of priority of U.S. Provisional Application No. 62/467,943, filed on Mar. 7, 2017. This and all other extrinsic materials discussed herein are incorporated by reference in their entirety.

FIELD OF THE INVENTION

The field of the invention is tritiated compounds.

BACKGROUND

The background description includes information that may be useful in understanding the present invention. It is not an admission that any of the information provided herein is prior art or relevant to the presently claimed invention, or that any publication specifically or implicitly referenced is prior art.

Present energy storage is substantially limited by the current chemical battery technology. This is due to both extensive infrastructure development over decades, and wide availability of components and materials in the commercial market. Chemical batteries have high power density, and can easily power most commercial devices for short time periods. However, they cannot withstand the test of time, when storing energy for more than a decade. In addition, chemical batteries suffer from charge leakage, temperature and environment sensitivity, and finite charge cycles.

Radioisotope batteries have the potential to fulfill these technical deficiencies. They are different from chemical batteries, because they are independent, self-containing energy sources using radioisotope decay. They produce consistent power over a widely-varied temperature range, meaning that they are not limited by diverse environmental conditions. Radioisotope batteries energy densities are also several orders of magnitudes greater than current chemical batteries. In general, then, radioisotope batteries have the theoretical ability to remedy deficiencies in current technologies, as well as introducing new operational capabilities, because of higher energy density, thermal and mechanical robustness, and a vastly longer lifetime compared to commercially available chemical batteries.

Isotopes decay through three types of particle emission: beta (electron or positron), alpha (atomic nucleus emission), and gamma (electromagnetic radiation). Beta emitting isotopes are the most appealing candidates for energy sources, as they do the least amount of harm to the semiconductor (converter) and to the environment. Beta-emitters are especially attractive fuel sources for use with sensitive electronics, since their high-energy electron emission has shallow penetration depth through the surrounding material.

Tritium and Nickel-63 have low energy beta emissions, are widely available in the commercial market, and have each been used for several battery prototypes. Tritium is the isotope of choice, since it is the least expensive per kilogram and kilojoule of all beta-emitting radioisotopes, low toxicity and is a low energy beta emitter with a half-life greater than 12 years.

Radioactive decay energy is converted to electrical energy using two main approaches: direct, charge collection, contact potential difference direct energy conversion (DEC), and indirect energy conversion (IDEC) through photovoltaics. The most efficient approach is the DEC configuration. In a two-dimensional perspective, the radioactive source is encapsulated or, in most situations, bonded to another compound called the carrier system. The layer(s) of encapsulated radioactive isotope emit beta particles (electrons) through the carrier system, hitting p-n junctions. Electron-hole pairs (e-h-ps, ehps, or EHPs) are produced in the surrounding semiconductor by the ionization trails of the beta particles. Use of low energy beta particles provide enhanced lifetimes, due to the absence of semiconductor degradations. The configuration can be compact, and can theoretically achieve the highest surface power density of all the energy conversion approaches.

In practice, however, DEC radioisotope batteries have suffered from major setbacks, including energy conversion efficiency, which is dependent on the semiconductor material, beta flux power, and effective density of the radioisotope. The inventive subject matter discussed herein address the latter two setbacks through improvements to the carrier system.

Prior art systems have energy densities that are too low to satisfy power requirements of most electronics. The metal hydrides have the highest specific activity and beta flux power. However, they suffer from numerous disadvantages common to all metal hydrides. First, there is low electron emission depth and beta self-absorption. Second, the known sources are unstable and brittle. Third, tritiated hydrides can ignite in contact with moisture, and with the exception of zirconium tritide and titanium tritide, known tritiated hydrides are pyrophoric. Known hydrides tend to be toxic. Finally, isotopic hydrides exhibit intrinsic leakage of the isotope, which leads to reduced power output, environmental hazard through radioactive contamination, and systemic failure.

Polymers can theoretically address some of the deficiencies of hydrides, but there is little promise for known tritiated polymers. Known tritiated polymers suffer from low effective energy densities, low specific activity, and are not radiation hardened due to weak binding energies. Carbons forms (carbon nanotubes, hydrogenated graphene, and graphane), which are state-of-the-art beta sources, have higher electron range depth and comparable specific surface activity to other hydrides. They could theoretically be used in isotope battery and fuel cell applications. However, there is not much experimental data to determine, if they are feasible on a micro- and macro-scale fabrication. In general, these tritiated carbon forms have to be made into films or foils due to beta self-absorption/stopping, which is dependent on the compound density. The larger systems are difficult to fabricate and heterogeneous with respect to isotope and carrier compound composition. In general, these geometric constraints severely limit the surface power density.

The known carrier systems for tritium are especially problematic for use in powering solid-state electronics, mobile devices, and sensors. The most promising approach is to select a carrier system that has low density, but comparable gravimetric density (wt % $^3H$) to tritiated metal hydrides. The beta source could be thicker, having greater electron range depth and still allow the beta particles to reach the converter. The figure of merit is the specific surface activity, which is the volume activity factoring in the electron range depth. Also, to further increase the overall power in the device, there must be greater interaction with the carrier and converter surfaces rather than just increasing the radioactivity per volume. If the configuration is planar, the beta source layers could be thick. If the configuration has a higher aspect ratio (e.g. converter is a honey-comb, trench, or pillared structure), the carrier is capable of coating the structure and filling in the open valleys and gaps, due to higher electron range depth.

U.S. Pat. No. 3,934,162, to Adler and Ducommon, describes a nuclear battery arranged in a fashion similar to a galvanic pile, with alternating layers of polymeric insulating material that demarcate "cells" of copper or Cr—Ni support for a beta-emitting radioactive material. Adler and Ducommon and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply. Unfortunately, the patent does not provide insight into the nature of suitable radioactive materials or how they may be formulated. U.S. Pat. No. 6,998,692, to Sanchez, teaches a radioactive power source resident in an IC package, but is similarly silent as to what beta emitter would suffice.

United States Patent Application Publication No. 2010/0204408 describes tritiated polymers for use as a radiation source in nuclear batteries having specialized porous semiconductor collectors. The described polymers are produced by tritiation of a polymer, such as poly(vinylacetylene). Due to the polymeric nature of these beta sources, it is necessary to apply these by wetting, using either melted or solvated polymer. It is not clear, however, if the resulting polymeric films are suitable for use conventional semiconductor materials, or how stable such tritiated polymers are.

One might question whether any of Cesium-137, Cobalt-60, Iodine-129, Iodine-131, Plutonium, Strontium-90 ($^{90}$Sr), Technetium-99, Nickel-63 ($^{63}$Ni), Phosphorus-33, Promethium-145, Promethium-146, Promethium-147, or Hydrogen-3 (tritium, $^3$H) would suffice, but each of these elements, per se, would have significant limitations when used in a Sanchez device, making them impractical as an energy source. Most of these beta emitter radioisotopes are not abundant, which in turn considerably increases the $/kJ making it not practical for mass production. And most emit high energy beta particles that could damage semiconductor convertor or other nearby sensitive electronics.

In addition, tritium is a gas at STP, which is difficult to control in a closed volume without a carrier system. The iodide isotopes, for example, are toxic, as are plutonium and strontium. $^{90}$Sr has a half-life of 28.8 years and has one of the lowest $/kJ. Yet, it is highly toxic to the environment and living organisms. It has an estimated 18-year half-life when absorbed into living tissue. It is considered a bone-seeker, which means the element or radioisotope will accumulate in the bones. It chemically behaves like calcium and will replace calcium, causing health risks such as bone cancer. Technetium has a half-life of 211,000 years, whereas the half-life of $^{131}$Iodine is only 8 days, both of which are impractical for construction of energy devices. The longer half-life radioisotopes, greater than 25 years, will reduce specific power and power density.

Thus, there is still a considerable need to provide a carrier system for a beta emitter that would be cost-effective, energy dense, non-toxic, and practical with respect to semiconductor and other applications.

SUMMARY OF THE INVENTION

The present invention provides apparatus, systems, and methods to tritiate nitroxides that are used as a beta emitter in a power source.

In one class of embodiments, tritiated nitroxides can be used for beta voltaic (βV) batteries. In such embodiments, tritium is the radioisotope and fuel source. In other applications and embodiments, hydrogen would replace tritium for hydrogen storage in fuel cells. For βV batteries, the beta source is implemented into a direct energy conversion (DEC) system, which can utilize dedicated semiconductor materials or conventional integrated circuits for generation of electrical power. In some integrated circuit implementation, the beta voltaic battery provides power for non-power generating functions of the integrated circuit utilized to generate electric power.

Inexpensive, practical, and convenient synthesis of nitroxide-based beta radiation source is provided. Use of a nitroxide provides a beta radiation source that is pliable or moldable into any desired shape, and which can be readily dissolved in a wide variety of organic solvents for application as a thin or thick film or as a powder, liquid, or paste. This flexibility allows it to be applied to any surface and form factor. Such a beta radiation source is able to achieve specific activity (high energy density) comparable to unstable metal hydrides and beta flux power with a mass density similar to polylactide (PLA). Lower density and molecular weight reduces beta absorption, allowing the use of relatively thick layers. This increases the radioactivity per unit volume. The attachment of the beta source with a semiconductor converter allows it to power electronic solid-state devices, mobile devices, medical devices, remote sensors, and spacecraft instruments for decades.

These and various other objects, features, aspects, and advantages of the inventive subject matter will become more apparent from the following detailed description of preferred embodiments, along with the accompanying drawing figures in which like numerals represent like components.

DETAILED DESCRIPTION

Inventors have found that nitroxides provide stable and readily synthesized sources of tritium-derived beta radiation. Such nitroxides can be provided as pliable and/or moldable solids that can be configured for a wide variety of applications, and are readily soluble in a wide variety of organic solvents to provide a solution for liquid application. Such liquid applications can be subsequently permitted to dry to provide a powder or powder coating. Inventors have found that such tritiated nitroxides are particularly suitable for use β radiation sources in nuclear batteries, for example as stable sources of β-radiation that can be readily applied to a semiconductor or photoelectric components of such nuclear batteries.

The following discussion provides example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Also, as used herein, and unless the context dictates otherwise, the term "coupled to" is intended to include both direct coupling (in which two elements that are coupled to each other and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Moreover, and unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

Described below are examples of tritiated nitroxide compounds, which can be used as carrier systems. In each case the carrier is a nitroxide group, which excluding the isotope is abundant and low cost with comparison to all other carrier compounds (e.g. metals, polymers, and carbon forms). The syntheses of the examples shown herein only require one or two steps. The resultant tritiated nitroxide is expected to be very stable. The compound can be scaled up, and have consistent tritium/hydrogen concentration during synthesis. The molecular weights of these tritium-containing nitroxides described below are g/mol. The compounds should have high, consistent yield of 9.4% tritium gravimetric density, specific activity range between 800 Ci/g to 900 Ci/g, and a mass density ranging from 0.1 $g/cm^3$ to 1.3 $g/cm^3$.

Figure 1:
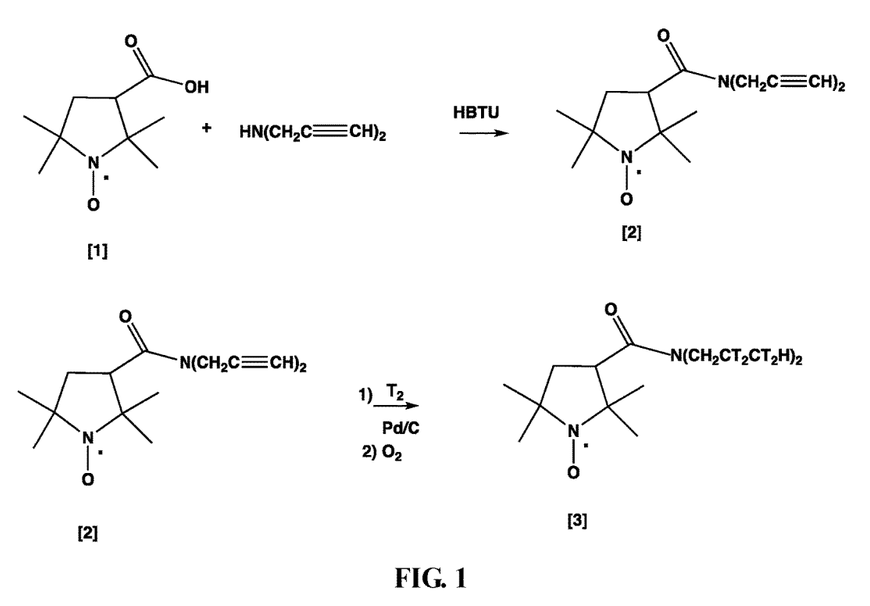
FIG. 1: Synthesis of a tritiated nitroxide (3), which is designed to be soluble in a wide variety of polar organic solvents.

Tritiated Di-n-propylamine Nitroxide (3) (FIG. 1)

In a 50 mL round bottom flask, containing dipropargylamine (0.2 gm, 2.1 mmol) dissolved in 5 mL DMF was added nitroxide (1) (0.5 gm, 2.5 mmol). Upon dissolution, HBTU (0.95 gm, 2.5 mmol) was added and the reaction was stirred at room temperature for 30 minutes. Then N,N-diisopropylethylamine (0.32 gm, 0.41 mL, 2.5 mmol) was added and the reaction was stirred at room temperature overnight. Thereafter, methylene chloride (50 mL) and a solution of citric acid (1 M, 10 mL) were added. Upon separating the layers, the methylene chloride layer was washed with a solution of sodium hydrogen carbonate (1 M, 25 mL). Upon separating the layers, the methylene chloride solution was dried over anhydrous sodium sulfate. Upon evaporation to dryness, the remaining oil was chromatographed using silica gel, eluting with chloroform:methanol (10:0.1 ratio). The product, nitroxide (2) was a yellow solid, which was recrystallized from boiling hexane with dropwise addition of dioxane. The resultant yellow powder had a mass spectrum of 261 g/mol, confirming nitroxide (2). Tritiated nitroxide (3) was obtained as described in Russo, et al., (Appl. Radiat. Iso. 125: 66-73, 2017).

Figure 2:
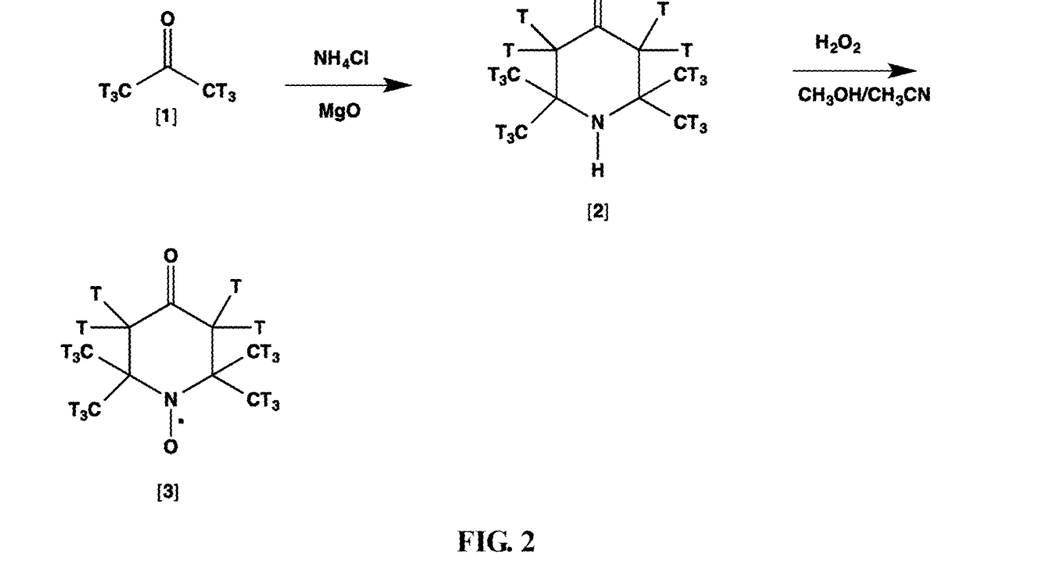
FIG. 2: Synthesis of a tritiated nitroxide (3), which is designed to be soluble in a wide variety of polar organic solvents.

4-Oxo-2,2,6,6-tetra($^3H_3$)methyl-(3,3,5,5-$^3H_6$)piperidine (6) (FIG. 2)

Ammonium chloride (3.5 gm, 65 mmol) was added to a 250 mL round bottom flask containing oven dried anhydrous sodium carbonate (3.18 gm, 30 mmol) and magnesium oxide (3 gm, 75 mmol). Then, tritium-substituted acetone (4, 20 mL) was introduced into the flask. After sealing the flask with a rubber septum, the reaction was heated to 50° C. in an oil bath for 3 days. Upon cooling, diethyl ether was added to the resulting solid, filtered, and the filter cake was crushed into a fine powder, washed with diethyl ether and filtered. This procedure was repeated two more times. The combined filtrates were evaporated to dryness in vacuo, affording a red liquid (5.35 gm) intermediate 4-Oxo-2,2,6,6-tetra($^3H_3$)methyl-(3,3,5,5-$^3H_6$)piperidine (5) (Tsai, et al., J. Org. Chem. 75: 6463-6467, 2010).

4-Oxo-2,2,6,6-tetra($^3H_3$)methyl-(3,3,5,5-$^3H_6$)piperidinyloxyl (6) (FIG. 2)

To a solution of crude 4-Oxo-2,2,6,6-tetra($^3H_3$)methyl-(3,3,5,5-$^3H_6$)piperidine (5) (5.35 gm, 2.86 mmol) dissolved in a mixture of methanol (35 mL) and acetonitrile (10 mL) was added sodium hydrogen carbonate (2 gm) and sodium tungstate (0.29 gm). Then, hydrogen peroxide (30%, 11 mL) was added, and the mixture was kept at room temperature for 2 days. Then, the reaction was filtered, and a saturated solution of sodium chloride (100 mL). Extraction with diethyl ether afforded, after drying with anhydrous magnesium sulfate, crude 4-Oxo-2,2,6,6-tetra($^3H_3$)methyl-(3,3,5, 5-³H₆)piperidinyloxyl (3). This compound was chromatographed, eluting with hexane/diethyl ether (4:1) to yield pure 4-Oxo-2,2,6,6-tetra(³H₃)methyl-(3,3,5,5-H₆)pipendinyloxyl (6), as red oil that solidified upon standing (2.9 gm, 51%) (Tsai, et al., J. Org. Chem. 75: 6463-6467, 2010).

Figure 3:
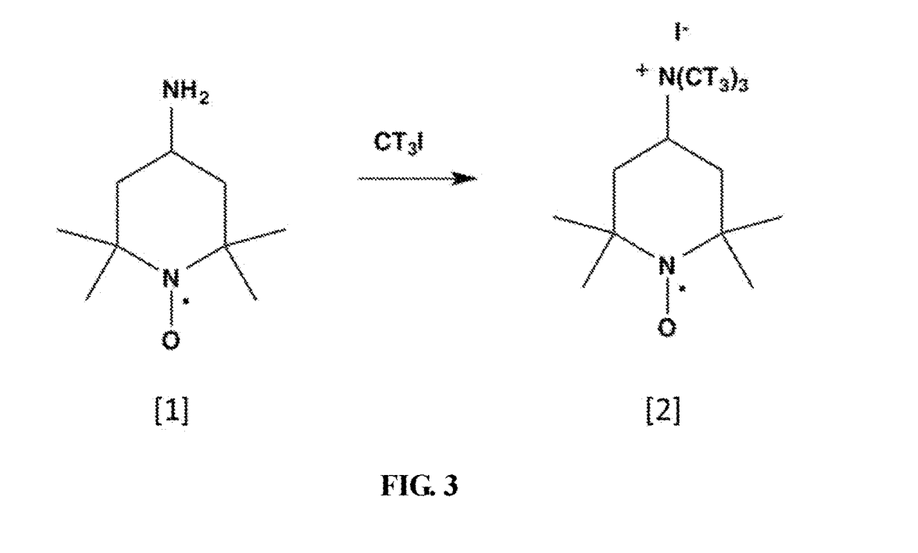
FIG. 3: Synthesis of a tritiated nitroxide (2), which is designed to be soluble in a wide variety of polar organic solvents.

N,N,N-Trimethyl(³H₉)-2,2,6,6-tetramethyl-1-piperidinyloxyl iodide (8) (FIG. 3)

Tritiated methyl iodide (0.68 gm, 4.6 mmol) was added to a solution of DMF (5 mL) of 4-amino-2,2,6,6-tetrametehyl-1-piperidinyloxyl (7) (0.17 gm, 1 mmol) and 4-hydroxy-2,2,6,6-tetramethyl-piperidine (0.31 gm, 2 mmol, Aldrich) at room temperature. The mixture is stirred until it becomes homogenous and then the solution is allowed to stand for 3 hr at room temperature. Crystals form, which are then filtered, and washed with diethyl ether giving nitroxide (8). (Rauckman, et. al. Org. Prep. Proc. Int. 9: 53-56, 1977; Eriksson, et al., J. Pharm. Sci. 75: 334-337, 1986).

The tritiated nitroxides (FIG. 1, (3)), (FIG. 2, (6)), and (FIG. 3, (8)) are stable and un-reactive when in contact with moisture. These nitroxides are not volatile, nor are they hazardous to the surrounding environment. In addition they are very pliable, and therefore easy to work with. Tritiated nitroxides are dissolvable in a variety of different organic solvents. Solutions of nitroxides can be prepared in various concentrations and layered over many surfaces by application of such a solution followed by evaporation of the solvent. Solutions of nitroxides can form into a thick (1 mm or more) film or a thin (less than 1 mm) film, and can be readily applied to semiconductor material, such as flat/planar, pillar, and/or trench/comb semiconductor structures.

Figure 4:
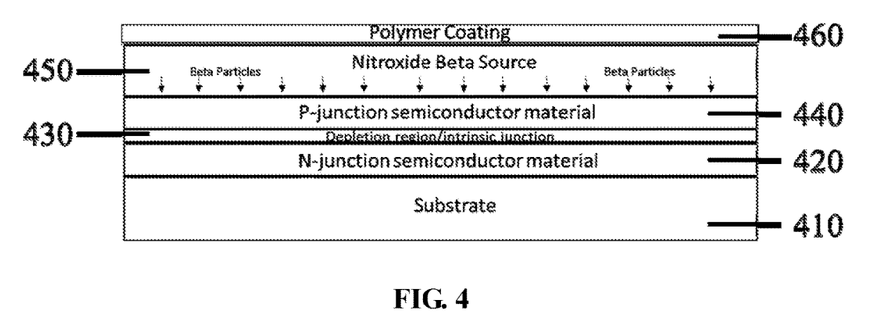
FIG. 4: is a cross-sectional view of the beta source coated or placed on top of a planar semiconductor structure with polymer coating placed on top of entire structure.

It is considered highly advantageous to encapsulate the tritiated nitroxide, so that the beta particles can be focused in a particular direction. The encapsulating material is preferably of a controlled thickness, and is able to conform to the various package contours. Furthermore, the material is preferably constructed so as to direct the beta emissions to the semi-conductor layers, rather than emit to the free surface. Such an arrangement is shown in FIG. 4. In FIG. 4, a substrate 410 supports the components of a typical semiconductor circuit, including an N-junction 420, a depletion region 430, and a P-junction 440. A tritium-containing nitroxide carrier 450 serves as a source of beta particle radiation that is directed to the P-junction 440 that is juxtaposed with one side of the nitroxide carrier 450. The remaining side of the nitroxide carrier 450 is covered with a polymer coating 460 that serves as an encapsulating layer.

The criteria for suitable encapsulating materials can be satisfied by various materials, such as polymers, and are conducive to film/sheet casting (for example, PLA). A polymer coating serving as an encapsulating layer preferably has a thickness in the range of about 50 μm to about 100 μm to focus substantially all beta particles in a particular direction. Another such coating can be a membrane material, which creates a dense, thin surface over the substrate. This denser layer can further reduce the emissions of the beta particles into the atmosphere, resulting in a higher rate to the semi-conductor junction. Exemplary membrane materials include cellulose acetate butyrate or other reverse osmosis-like membranes which, under heating, create a dense skin. Manufacture of these coatings can alternatively be achieved by various other methods, according to the specific material and application. For example, the polymer coatings can be film cast, applied under vacuum, shrink wrapped, and/or sprayed.

Through βV DEC, such a device can generate consistent power for two or more decades. Such a battery can be used, for example, to power terrestrial and/or space-based electronic devices, due to its robustness and high energy density. Such a battery can power remote sensors for 10 to 20 years without replacement or maintenance. For space applications, which can last 15 to 25 years, a tritium battery (being both thermally and mechanically robust) can be used to power onboard electronics consistently and reliably. A tritium-based battery can have one of the highest βV DEC battery densities compared to other beta emitting radioisotopes. In various embodiments, a tritium-containing compound can be placed or coated onto planar, trenched, pillared, and/or honeycombed semiconductor structures, as shown in FIGS. 4 to 7. In some embodiments the surface of tritiated compound that is not juxtaposed with the semiconductor can be sealed, for example by a polymer film or thin coating, as shown in FIGS. 4 to 10.

Figure 5:
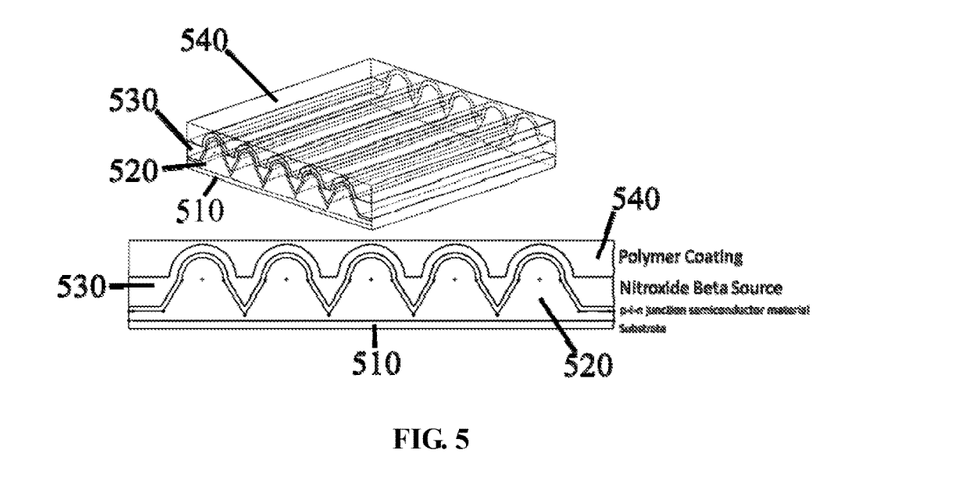
FIG. 5: is a cross-sectional view of the beta source coated or placed on top of an etched semiconductor surface (trenched structure).

As noted above, various configurations can be used to increase the area available for interaction between a beta-emitting material and a semiconductor of a nuclear battery of the inventive concept. FIG. 5 shows an embodiment of the inventive concept in which a substrate 510 supports p-i-n semiconductor material 520 that is arranged in a repeating raised semicircular pattern, which provides increased surface area for interaction with beta particles. These features can be produced by any suitable means, including trenching, cutting, and/or etching. A nitroxide beta source 530 is provided as a layer over the semiconductor material 520, with the opposing side of the nitroxide beta source 530 covered by a polymer coating encapsulating layer 540 configured to block release of beta radiation to the environment and direct beta radiation towards the semiconductor material 520.

Figure 6:
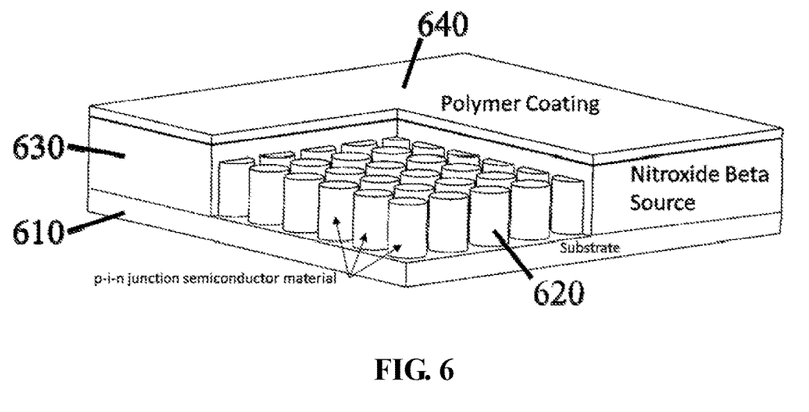
FIG. 6: is a cross-sectional view of the beta source coated or placed on top of an etched semiconductor surface (pillared structure).

FIG. 6 shows an alternative embodiment of the inventive concept in which a substrate 610 supports p-i-n semiconductor material 620 that is arranged in a repeating pattern of projecting pillars, which provides increased surface area for interaction with beta particles. Although depicted as having a circular cross section, such pillars can have a hexagonal cross section, partially circular cross section, polygonal cross section, and or irregular cross section. In some embodiments a pillar of semiconductor material can have a consistent cross section along its major axis. These features can be produced by any suitable means, including trenching, cutting, and/or etching. In other embodiments a pillar of semiconductor material can vary in shape and/or dimension along its major axis. A nitroxide beta source 630 is provided as a layer over and between the pillars of semiconductor material 620, with the external (i.e. oriented away from the substrate) surface of the nitroxide beta source 630 covered by a polymer coating encapsulating layer 640 configured to block release of beta radiation to the environment.

Figure 7:
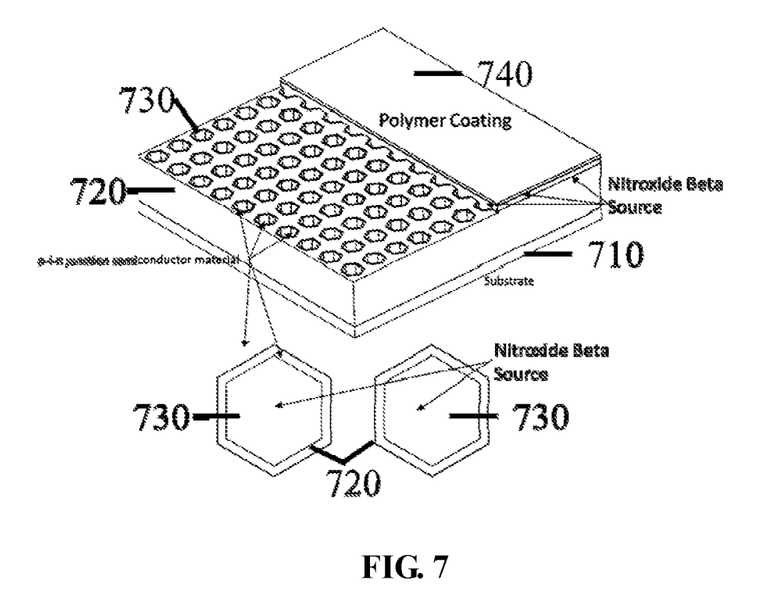
FIG. 7: is a top view of the beta source coated or placed in semiconductor material (honey-combed structure).

FIG. 7 shows another alternative embodiment of the inventive concept in which a substrate 710 supports p-i-n semiconductor material 720 that is arranged in a repeating pattern of columns having an open interior, which provides increased surface area for interaction with beta particles. Although depicted as having a hexagonal cross section, such columns can have a circular cross section, partially circular cross section, polygonal cross section, and or irregular cross section. In some embodiments a column of semiconductor material can have a consistent cross section along its major axis. In other embodiments a column of semiconductor material can vary in shape and/or dimension along its major axis. These features can be produced by any suitable means, including trenching, cutting, and/or etching. A nitroxide beta source 730 is provided as a layer that extends into the interior of the columns of semiconductor material 720. with the external (i.e. oriented away from the substrate) surface of the nitroxide beta source 730 covered by a polymer coating encapsulating layer 740 configured to block release of beta radiation to the environment.

Figure 8:
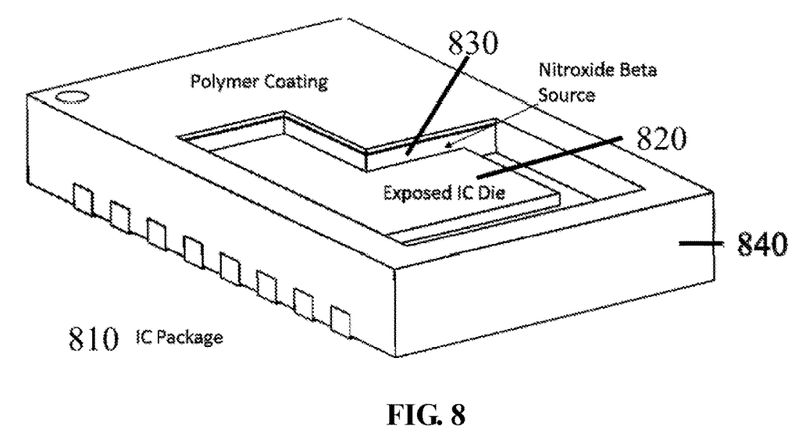
FIG. 8: is perspective or isometric view with a partial cut out of the beta source coated or placed on top of IC package to power existing device.
Figure 9:
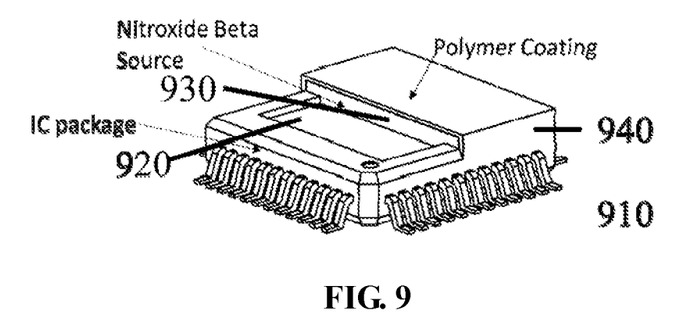
FIG. 9: is perspective or isometric view with a partial cut out of the beta source coated on top of expose IC die for direct onboard power.
Figure 10:
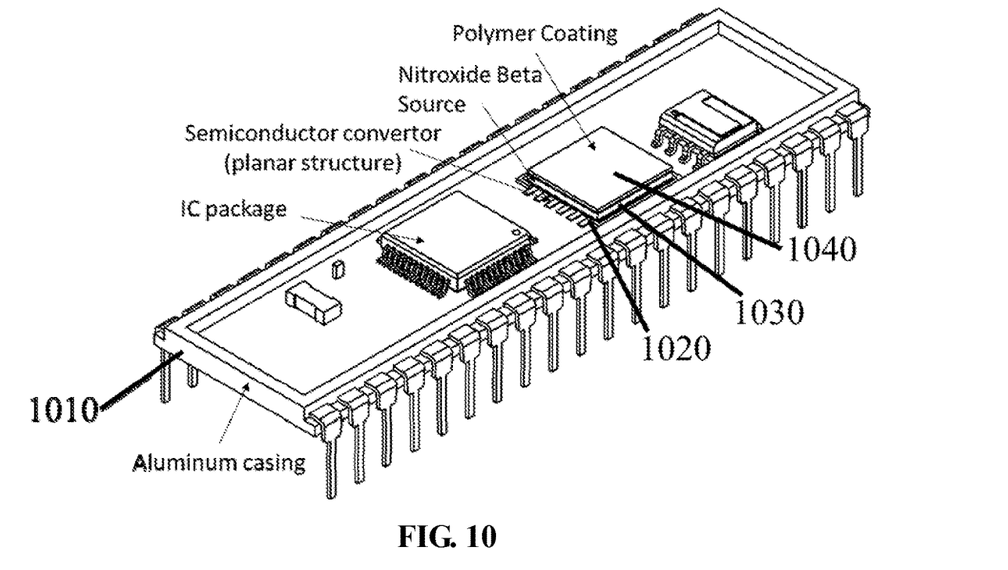
FIG. 10: is perspective or isometric view with a partial cut out of the beta source coated on semiconductor material with supercapacitor in IC and DIP package.

The Inventors have noted that integrated circuits can provide an abundance of semiconductor circuits suitable for generation of electric power on exposure to beta radiation. In some applications, a beta radiation emitting carrier system, by itself, can be placed on or near (or, alternatively, coated onto) an exposed IC chip die or other silicon and gallium arsenide IC chips for onboard power, as shown in FIGS. 8 to 10. Such compounds as described above are deformable and can be easily applied on any surface and aspect ratio. The relatively non-penetrating low energy beta radiation provided supports simple implementation on existing circuits. Such a beta source can provide direct power on an exposed commercial available IC chip, as shown in FIGS. 8 to 10. After the tritium-containing compound is applied to the surface an additional layer of polymer can be used to seal the beta radiation source and exposed side of the IC chip. Such an arrangement can be applied to a wide variety of electronic devices (such as sensors) to improve efficiency by powering the microprocessors sleep mode without draining the primary battery.

An example of such an embodiment is shown in FIG. 8. As shown, an integrated circuit package 810 can support an exposed integrated circuit die 820 that includes semiconductor materials capable of generating electrical power when exposed to beta radiation. A nitroxide beta radiation source 830 of the inventive concept can be applied directly to the exposed die 820 to provide such beta radiation. The beta radiation source 830 and any exposed integrated circuit die 810 can be encapsulated with a polymer coating 840, preventing emission of beta radiation into the environment and directing it towards the semiconductors of the die 820. Such an embodiment can be used as a power source for powering other elements of a device, and/or be utilized to power functions of the integrated circuit package itself.

A similar embodiment is shown in FIG. 9. As shown, an integrated circuit package 910 can support an exposed integrated circuit die 920 that includes semiconductor materials capable of generating electrical power when exposed to beta radiation. A nitroxide beta radiation source 930 of the inventive concept can be applied directly to the exposed die 920 to provide such beta radiation. The beta radiation source 930 and any exposed integrated circuit die 920 can be encapsulated with a polymer coating 940, preventing emission of beta radiation into the environment and directing it towards the semiconductors of the die 920. Such an embodiment can be used as a power source for powering other elements of a device, and/or be utilized to power functions of the integrated circuit package itself.

As shown in FIG. 10, in some embodiments of the inventive concept a small, compact nuclear battery can be provided on a common substrate to power one or more associated integrated circuits. As shown, an aluminum casing 1010 supports a nuclear battery of the inventive concept that includes a semiconductor converter 1020 (for example, an integrated circuit that includes semiconductors) that is juxtaposed with a nitroxide beta radiation source of the inventive concept 1030. A polymer coating 1040 serves to encapsulate the nitroxide beta radiation source 1030 and direct beta radiation towards the semiconductor converter 1020. Electrical power produced by this compact nuclear battery can be used to power circuitry of the semiconductor converter 1020 and/or at least one other integrated circuit 1050 provided in or on the same casing 1010.

Such a βV DEC battery, depending on radioisotope and semiconductor material quantity, can power solid state electronics, mobile devices, medical implants like pacemakers and hearing aids, and/or security systems, and/or serve as a trickle charger for a primary battery of such devices. The battery could be directly placed on the circuit as onboard power for sensor sleep mode or active mode. The battery would be electronically and mechanically connected to the circuit board. The battery would resemble a basic dual in-line package or surface mount IC chip. The batteries have the potential to be maintenance free power sources for remote, long term, low power sensors. Because current sensors' microprocessors have low quiescent power requirement for sleep mode ranging from 1-10 μW, a small quantity of material (beta source and semiconductor) is able to continuously power sensor throughout its entire lifetime. The power source will have a lifetime of the sensor network or infrastructure rather than itself. This could introduce widespread intelligent sensor networks that could monitor large amounts area of diverse environments and have the constant power to rely important information back using communicate nodes. This type of capability is extremely useful for private companies and defense agencies that need this information in violent or remote areas without generated logistic obstacles.

Another embodiment of tritiated nitroxides involves beta source (carrier system) mixed with phosphor interacting with commercially available or custom design photovoltaic solar cells. Indirect energy conversion (IDEC) is converting nuclear decay of optical energy to electrical energy. They are also called beta-photovoltaics (β-PV) cells. The beta decay excites the phosphor generating photon emission usually at a narrow wavelength bandwidth.

Radioluminescence is directly impacted by the decay energy spectrum and phosphor chemical composition. Current IDEC systems use two-dimensional, planar interactions with beta source and phosphor and phosphor and photovoltaic. In tritium based light source or IDEC systems, the tritium gas is either pressurized and encapsulated inside a phosphor lined glass vial or chemically bonded to a thin organic polymer or hydride, and then coated onto the surface of phosphor particles.

In β-PV cells of the inventive concept a beta source (e.g. a tritiated nitroxide, as described above) can be mixed with a phosphor compound in a slurry and dried into a powder. This advantageously increases the interaction with isotope and phosphor. Suitable phosphors include ZnS:Cu and $SrAl_2O_4:Eu^{2+},Dy^{3+}$, which have a peak emission wavelength of about 520 nm, i.e. green light (2.2 eV). The beta source/phosphor mixture can be applied to an active surface of a photovoltaic device (for example, a photovoltaic device having a two-dimensional configuration) and dried to a powder through room temperature evaporation. In some embodiments, to increase surface aspect ratio between a photovoltaic and a beta source/phosphor mixture, III-IV generation nanopillar solar cells can be used as an optical to electrical energy converter. In such embodiments a beta source/phosphor slurry can fill within gaps between the pillars or wires of the solar cell, and can also be applied to the top surface. Nanopillars increase contact area with beta-loaded phosphor light source. Such nanopillars can include a anti-reflection coating to improve the efficiency of conversion, can act as efficient light absorbers with improved light trapping and absorption than conventional planar solar cells, and can provide higher current and more effective carrier collection. In some embodiments GaAs and/or InGaP solar cells can be used in order to provide a bandgap that matches the optical phosphor output.

Thus, specific compositions and methods of tritiated nitroxides have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A tritiated nitroxide, comprising:
one or more atoms of
and a nitroxide bearing five membered core structure wherein R10 to R17 are each either hydrogen or tritium, and
wherein at least one of R10 to R17 is tritium.

2. The tritiated nitroxide of claim 1, wherein the tritiated nitroxide comprises at least 8 tritium atoms, and has a specific activity of 800 Ci/g to 900 Ci/g.

3. The tritiated nitroxide of claim 1, wherein the tritiated nitroxide includes at least 16 tritium atoms, and has a specific activity of 2370 Ci/g to 2526 Ci/g.

4. A power source comprising a beta radiation source and a power converter, wherein the beta radiation source comprises the tritiated nitroxide of claim 1, and wherein the power converter is positioned to receive beta radiation from the beta radiation source.

5. The power source of claim 4, wherein the beta radiation source comprises:
one or more atoms of tritium and
and a nitroxide-bearing five membered core structure wherein R10 to R17 are tritium, and
wherein at least one of R10 to R17 is tritium.

6. The power source of claim 5, wherein the beta radiation source is provided as film or layer applied to a surface of the power converter.

7. The power source of claim 6, further comprising an encapsulation layer, wherein the encapsulation layer encloses at least a portion of the beta source and the power converter.

8. The power source of claim 7, wherein the encapsulation layer comprises a polymer layer applied to at least a portion of the beta radiation source.

9. The power source of claim 4, wherein the power source is configured as a primary battery or power source.

10. The power source of claim 4, wherein the power source is configured as a secondary battery or a trickle charging device for the primary battery.

11. The power source of claim 4, wherein the power converter comprises a photovoltaic cell and a phosphor, wherein the phosphor is positioned to receive beta radiation from the beta radiation source and the photovoltaic cell is positioned to receive a photon from the phosphor.

12. The power source of claim 4, wherein the energy converter comprises a semiconductor positioned to receive beta radiation from the beta radiation source.

13. The power source of claim 4, wherein the power source comprises an integrated circuit.

14. The power source of claim 13, wherein the semiconductor forms part of an integrated circuit, and wherein current generated by the power source provides power utilized by the integrated circuit.

15. A method of producing a tritiated nitroxide of Formula 3 comprising:
contacting a compound of Formula 3

Formula 1 with dipropargylamine in the presence of HBTU and N,N'-diisopropylethylamine to produce a compound of Formula 2

Formula 2 contacting the compound of Formula 2 with a platinum catalyst and tritium to produce a compound of Formula 3

Formula 3

16. A method of manufacturing a power source comprising:
dissolving a tritiated nitroxide of claim 1 in a solvent to produce a solvated tritiated nitroxide;
applying the solvated tritiated nitroxide a surface of a power converter; and
removing the solvent from the solvated tritiated nitroxide so applied,
thereby forming a film or layer of the tritiated nitroxide on the surface of the power converter.

17. The method of claim 16, wherein the film or layer has a thickness of 1 mm or more.

18. The method of claim 16, wherein the film or layer has a thickness of less than 1 mm.

19. The method of claim 16, further comprising the step of applying an encapsulation layer to least a portion of the film or layer and the power converter.

20. The method of claim 19, wherein the encapsulation layer comprises a polymer layer.

21. The method of claim 16, wherein the power converter comprises a photovoltaic cell and a phosphor, wherein the phosphor is positioned to receive beta radiation from the beta radiation source and the photovoltaic cell is positioned to receive a photon from the phosphor.

22. The method of claim 16, wherein the energy converter comprises a semiconductor positioned to receive beta radiation from the beta radiation source.

23. The method of claim 22, wherein the semiconductor forms part of an integrated circuit.

* * * * *